United States Patent [19]
Sakata et al.

[11] Patent Number: 5,923,415
[45] Date of Patent: Jul. 13, 1999

[54] APPARATUS AND METHOD FOR MEASURING LONGITUDINAL MODULUS OF ELASTICITY OF FIBERS USED FOR COMPOSITE MATERIALS

[75] Inventors: Masaru Sakata, Yokohama; Hisaichi Ohnabe, Tokorozawa, both of Japan

[73] Assignee: Ishikawajima-Harima Heavy Industries Co., Ltd., Tokyo, Japan

[21] Appl. No.: 08/917,494

[22] Filed: Aug. 26, 1997

[30] Foreign Application Priority Data

Aug. 28, 1996 [JP] Japan .................................. 8-226427

[51] Int. Cl.$^6$ .................................................. G01N 21/84
[52] U.S. Cl. ............................................ 356/73.1; 73/160
[58] Field of Search .................... 73/160, 828; 356/73.1, 356/387, 429, 385

[56] References Cited

U.S. PATENT DOCUMENTS

| | | | |
|---|---|---|---|
| 4,976,191 | 12/1990 | Suzumori et al. | 92/48 |
| 5,167,150 | 12/1992 | Shofner et al. | 73/160 |
| 5,203,206 | 4/1993 | Shofner et al. | 73/160 |
| 5,268,158 | 12/1993 | Paul, Jr. | 423/447.1 |

OTHER PUBLICATIONS

Soviet Inventions Illustrated Section R, Week C11, London: Derwent Publication Ltd., R16; & SU 670851.
Database WPIL on Questel, Week 9710, London: Derwent Publications Ltd., AN 97–104714; & JP 08–338795 A.
"Strength Data Book" edited by strength design data book edition committee, Shokabo, 1962, p. 348.

*Primary Examiner*—Frank G. Font
*Assistant Examiner*—Tu T. Nguyen
*Attorney, Agent, or Firm*—Griffin, Butler, Whisenhunt & Szipl, LLP

[57] ABSTRACT

There is provided an apparatus for measuring a longitudinal modulus of elasticity of a fiber used for composite material, including a holder for supporting a single fiber at its one end in a cantilever fashion, a heater for heating the single fiber, a measurement device for measuring deflection of the single fiber, and a calculator for calculating a longitudinal modulus of elasticity of the single fiber in accordance with a deflection measured by the measurement device, provided that the single fiber is equivalent to a beam receiving uniformly distributed load thereon based on a dead weight thereof. For instance, the heater includes a closed container having a transparent window through which the deflection of the single fiber is measured The measurement device is a laser displacement gauge or an optical displacement gauge. The apparatus makes it possible to readily and rapidly measure a longitudinal modulus of elasticity of a single fiber in various temperatures including room temperature by using only a single fiber.

16 Claims, 3 Drawing Sheets

D1: INITIAL CONDITION BEFORE DEFLECTION

D2: DEFLECTION CONDITION DUE TO DEAD WEIGHT

D1: INITIAL CONDITION BEFORE DEFLECTION

D2: DEFLECTION CONDITION DUE TO DEAD WEIGHT

APPARATUS AND METHOD FOR MEASURING LONGITUDINAL MODULUS OF ELASTICITY OF FIBERS USED FOR COMPOSITE MATERIALS

BACKGROUND OF THE INVENTION

1. Field of the Invention

The invention relates to an apparatus and method for measuring a longitudinal modulus of elasticity of a fiber to be used for composite materials, such as Nickaron, Tyrano, SCS-6 and Nextel.

2. Description of the Related Art

These days, carbon fibers are widely used to reinforce polymer matrix composites (PMCs). In addition to PMCs, and metal matrix composites (MMCs) reinforced by continuous fibers, ceramic matrix composites (CMCs) have been researched and developed by using ceramic continuous fibers. In particular, continuous ceramic fiber such as Nickaron, Tyrano, SCS-6 and Nextel have been developed as reinforcing fibers for CMCs.

A longitudinal modulus of elasticity or Young's modulus of those continuous fibers having high stiffness has been conventionally measured in accordance with, for instance, a carbon fiber testing method defined in JIS-R7601. This method includes the steps of taking a single fiber out of samples one by one, adhering the single fiber at its opposite ends onto a sheet having an opening, recording a load-elongation curve by means of a tensile tester, and calculating the longitudinal modulus of elasticity E based on the gradient of the load-elongation curve in accordance with an appropriate equation.

The above mentioned conventional method is simple in principle, and hence can be applied to a wide range of fibers, but has problems that measurement procedure is complicated and that actual measurement takes much time. It is quite important in order to use these fibers in a composite material to measure the longitudinal modulus of elasticity E at a high temperature. However, it is quite difficult to hold a fiber at a high temperature, and in addition, large-scaled equipments and complicated, time-consuming measurement procedure are required to obtain a load-elongation curve at a high temperature in the above mentioned conventional method. Furthermore, the conventional method has another problem that since many test fibers are consumed for obtaining test data, a lot of test fibers have to be prepared for each of the test temperatures.

In particular, when fibers are used for composite material, the above mentioned conventional method has problems as follows.

First, rupture strain of the ceramic fibers is in the range of about 0.5 to 2 %, which are remarkably smaller than those of the other fibers. Thus, since a small misalignment in the fiber arrangement and a small difference in elongation among the fibers exert great influence on the measurement, and furthermore since the fiber is broken with a quite small load, it is quite difficult or almost impossible to exactly measure the longitudinal modulus of elasticity E of the fiber.

Second, since the fibers are brittle, they are likely to be broken at a portion at which they are grasped by a tensile tester during carrying out a tensile test. Fibers are not likely to fracture within a gauge length in which rupture of fibers is expected to occur.

SUMMARY OF THE INVENTION

In view of the foregoing problems of the conventional methods, it is an objective of the present invention to provide an apparatus and a method both capable of readily and rapidly measuring a longitudinal modulus of elasticity E of fibers used for composite material at various temperatures as well as room temperature by using only a single fiber.

In one aspect, there is provided an apparatus for measuring a longitudinal modulus of elasticity of a fiber used for composite material, including a holder for supporting a single fiber at its one end in a cantilever fashion, a heater for heating the single fiber, a measurement device for measuring deflection of the single fiber, and a calculator for calculating a longitudinal modulus of elasticity of the single fiber in accordance with the deflection measured by the measurement device, assuming that the single fiber is equivalent to a beam receiving uniformly distributed load thereon by the dead weight thereof.

In accordance with the above mentioned apparatus, a single fiber is carried by the holder in a cantilever fashion, and gradually heated by the heater. Then, deflection of the fiber is measured by means of the measurement device. A longitudinal modulus of elasticity E of the fiber can be obtained based on the thus measured deflection. Thus, it is now possible to readily and rapidly measure a longitudinal modulus of elasticity E at various temperatures including room temperature by using only a single fiber.

The heater may include a closed container having a transparent window through which the deflection of the single fiber is measured by the measurement device. The closed container may be filled with inert gas or atmospheric air, by which a fiber is avoidable from degradation.

A laser displacement gauge or an optical displacement gauge may be employed as the measurement device. Those gauges make it possible to correctly measure the deflection of each of portions of a single fiber as well as the deflection of a tip end.

It is preferable for the calculator to include a compensator for compensating for the initial deformation of the single fiber. For instance, the compensator is designed to eliminate the initial deformation of the single fiber by defining the deflection $\Delta$ of the single fiber in accordance with the following equation:

$$\Delta = (Y_1 + Y_2)/2$$

where $Y_1$ represents the deflection of the single fiber measured when a plane containing the single fiber therein makes an angle A degrees with a vertical direction, and $Y_2$ represent deflection of the single fiber measured when the plane makes an angle $(A+180)$ degrees with a vertical direction. For instance, the angle A is pre-set to be 0 degree.

In another aspect, there is provided a method of measuring a longitudinal modulus of elasticity of a fiber used for composite material, including the steps of (a) supporting a single fiber at its one end in a cantilever fashion, (b) heating the single fiber, (c) measuring the deflection of the single fiber, and (d) calculating a longitudinal modulus of elasticity of the single fiber in accordance with the deflection measured in the step (c), assuming that the single fiber is equivalent to a beam receiving uniformly distributed load thereon based on dead weight thereof.

The method preferably includes the additional step (e) of filling the closed container with inert gas before measuring deflection of the single fiber.

The method preferably includes the additional step (f) of compensating the initial deformation of the single fiber. The step (f) is to be carried out subsequently to the step (d). For instance, the initial deformation of the single fiber is eliminated in the step (f) by defining deflection $\Delta$ of the single fiber in accordance with the following equation:

$$\Delta = (Y_1 + Y_2)/2$$

wherein $Y_1$ represents the deflection of the single fiber measured when a plane containing the single fiber therein makes an angle A degrees with the vertical direction, and $Y_2$ represents the deflection of the single fiber measured when the plane makes an angle (A+180) degrees with the vertical direction.

The above and other objects and advantageous features of the present invention will be made apparent from the following description made with reference to the accompanying drawings, in which like reference characters designate the same or similar parts throughout the drawings.

DESCRIPTION OF THE PREFERRED EMBODIMENT

A preferred embodiment in accordance with the present invention will be explained hereinbelow with reference to the drawings.

Figure 1:
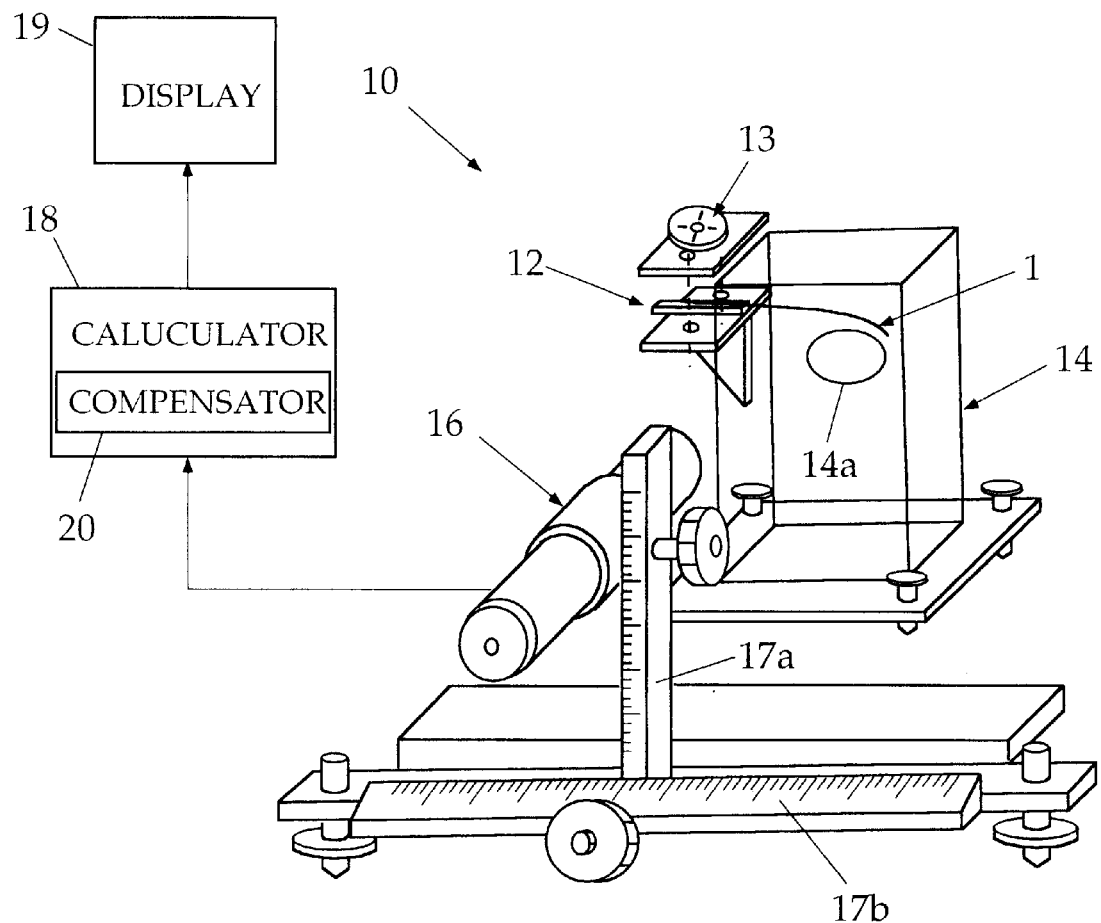
FIG. 1 is a perspective view illustrating an apparatus made in accordance with the present invention for measuring a longitudinal modulus of elasticity E of a fiber used for composite material.

As illustrated in FIG. 1, an apparatus 10 for measuring a longitudinal modulus of elasticity of a fiber used for composite material includes a holder 12 for supporting a single fiber 1 at its one end in a cantilever fashion, a heater 14 for heating the single fiber 1, a deflection measurement device 16 for measuring the deflection of the single fiber 1, and a calculator 18 for calculating a longitudinal modulus of elasticity of the single fiber 1 in accordance with the deflection measured by the deflection measurement device 16, assuming that the single fiber 1 is equivalent to a beam receiving uniformly distributed load thereon based on dead weight thereof.

The fiber holder 12 is equipped with a level 13 for exactly horizontally supporting the single fiber 1.

The heater 14 is comprised of a closed container having a transparent window 14a through which the deflection of the single fiber 1 is measured by the deflection measurement device 16. The closed container 14 is filled with inert gas or atmospheric air. The closed container 14 is equipped therein with a thermocouple (not illustrated) for measuring and controlling the temperature in the closed container 14. The arrangement as mentioned above makes it possible to measure the deflection of the single fiber 1 through the transparent window 14a of the heater 14 at various temperatures including the room temperature by using a single fiber as the temperature in the closed container 14 is gradually increased.

The deflection measurement device 16 is comprised of a laser displacement gauge or an optical displacement gauge.

As illustrated in FIG. 1, the deflection measurement device 16 is fixed to a vertical mover 17a which is capable of vertically moving inch by inch and which is fixed to a horizontal mover 17b which is capable of horizontally moving inch by inch. Thus, the deflection measurement device 16 is vertically and horizontally movable to a desired position so that the device 16 is always in alignment with the transparent window 14a of the heater 14. By means of the deflection measurement device 16, it is possible to readily, rapidly and exactly measure the deflection of each part of the single fiber 1, for instance, the deflection of a tip end of the single fiber 1.

Figure 2:
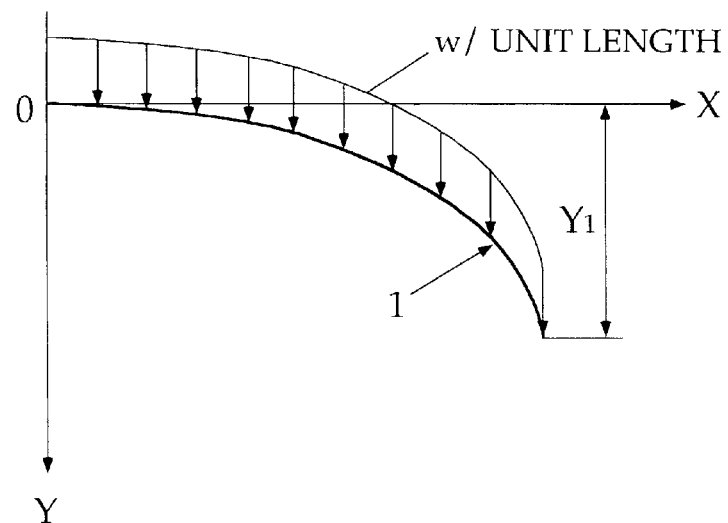
FIG. 2 is a schematic view for explaining the principle of the present invention, illustrating a beam under uniform distributed load thereon.

Signals representing the deflection measured with the device 16 are transmitted to the calculator 18. Such signals may be transmitted to the calculator 18 manually by an operator. The calculator 18 analyzes the single fiber 1 deflected by the dead weight of itself, assuming that the single fiber is equivalent to a beam receiving uniformly distributed load thereon as illustrated in FIG. 2. Since the deflection of a single fiber supported in a cantilever fashion cannot be deemed as a small deflection relative to the length of a single fiber, the deflection Y of the single fiber 1 corresponds to so-called large deflection.

Deflection $Y_1$ at a tip end of the single fiber 1 is defined in accordance with the equation (1). Thus, by measuring the deflection $Y_1$ of the single fiber 1, v can be determined in accordance with the equation (1). Herein, v is defined in accordance with the equation (2), and hence, a longitudinal modulus of elasticity E of the single fiber 1 can be calculated in accordance with the equation (3) transformed from the equation (2). If the single fiber 1 has a circular cross-section, a longitudinal modulus of elasticity E of the single fiber 1 can be calculated in accordance with the equation (4).

$$Y_1 = Lv(1-v^2/80)/8 \tag{1}$$

$$v = wL^3/EI \ (0 \leq v \leq 2.5) \tag{2}$$

$$E = wL^3/vI \tag{3}$$

$$E = 16\rho L^3 g/d^2 v \tag{4}$$

In these equations, E represents the longitudinal modulus of elasticity or Young's modulus, I represents the moment of inertia of the cross-section, w represents the load caused by the weight per unit length of the fiber, L represents the entire length of the fiber, d represents the diameter of the fiber, ρ represents the density of the fiber, $Y_1$ represents the deflection at the tip end of the fiber in the Y-axis direction, and g represents the gravitational acceleration. A diameter "d" of the fiber in the equation (4) can be accurately measured by means of a scanning electron microscope, and the density "ρ" of the fiber in the equation (4) can be calculated, for instance, based on weight and diameter. The equations (1) and (2) are quoted from "Strength Data Book" edited by strength design data book edition committee and published through Shokabo, 1962, p 348.

The calculator 18 receives the signals representing the deflection $Y_1$ at the tip end of the single fiber 1, and calculates the longitudinal modulus of elasticity of the single fiber 1 in accordance with the equations (1) to (4). The thus calculated longitudinal modulus of elasticity E of the single fiber 1 is displayed at a screen 19.

Figure 3A:
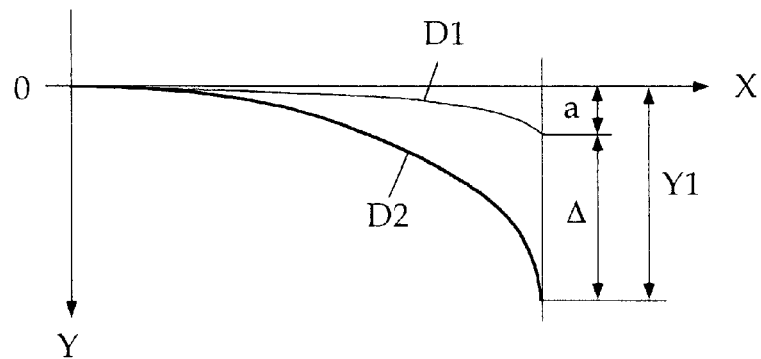
FIGS. 3A and 3B are schematic views for explaining how to eliminate the initial deformation of a fiber, each illustrating a beam having the initial deformation without uniform load thereon and with uniform load thereon.

A single fiber often has an initial deformation "a", as illustrated in FIG. 3A. Deflection Δ caused by the dead weight of a single fiber having an initial deformation "a" can be represented by the equation (5):

$$\Delta = (Y_1 + Y_2)/2 \tag{5}$$

wherein $Y_1$ represents the deflection of a single fiber measured when a plane containing the single fiber therein makes an angle A degrees with the vertical direction, and $Y_2$ represents the deflection of the single fiber measured when the plane makes an angle (A+180) degrees with the vertical direction. That is, the initial deformation "a" directs oppositely to each other when a plane containing the single fiber therein makes an angle A degrees (FIG. 3A) and an angle (A+180) degrees (FIG. 3B) with a certain direction such as the vertical direction. Hence, it is possible to eliminate influence exerted by the initial deformation "a" by adopting the average Δ of the deflection as the deflection $Y_1$ of the single fiber 1.

Figure 3B:
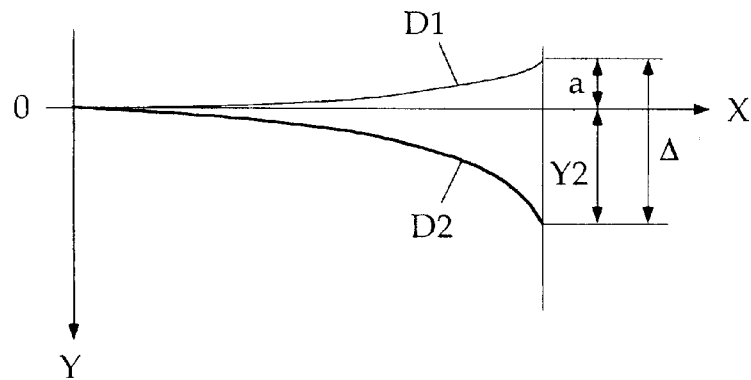

In view of the foregoing discussion, the calculator 18 includes a compensator 20 for compensating for the initial deformation "a" of the single fiber 1. The calculator 18 receives a signal from the deflection measurement device 16 which represents the vertical deflection $Y_1$, as illustrated in FIG. 3A. Then, the calculator 18 also receives a signal from the deflection measurement device 16 which represents the vrtical deflection $Y_2$ when the fiber is rotated by 180 degrees, as illustrated in FIG. 3B. The compensator 20 constituting a part of the calculator 18 calculates the average Δ of the deflection in accordance with the equation (5). The calculated average Δ is returned back to the calculator 18, which then calculates the longitudinal modulus of elasticity E of the single fiber in accordance with the equations (1) to (4). The calculation result is displayed at the screen 19.

Figure 4:
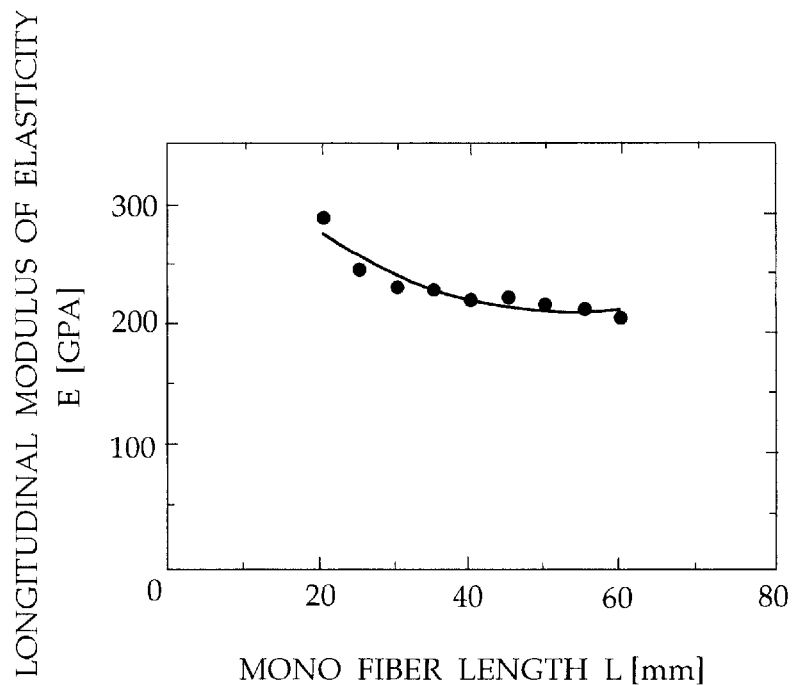
FIG. 4 is a graph showing a longitudinal modulus of elasticity vs. fiber length curve.

FIG. 4 shows the result of the experiments having been conducted on the apparatus 10 illustrated in FIG. 1. FIG. 4 shows a typical case among the experiments having been conducted at room temperature with the length of the fiber being varied. The experimental results show that the longitudinal modulus of elasticity continuously varies with the fiber length. This is considered because a diameter is not uniform even in a single fiber, and continuously varies with the fiber length. Accordingly, a longitudinal modulus of elasticity E of a tested fiber can be determined based on an average of varied values obtained by experiments. The experiments were conducted at room temperature, but it should be noted that the longitudinal modulus of elasticity E at various temperatures as well as at room temperature can be determined by using a single sample fiber by means of the heater 14.

As described in connection with the preferred embodiment, in accordance with the present invention, a single fiber is supported at its one end by a fiber holder in a cantilever fashion, and the deflection of the fiber is measured with the fiber being gradually heated by a heater. The longitudinal modulus of elasticity E of the fiber can be determined based on the measured deflection in accordance with the above mentioned equations (1) to (5).

An apparatus made in accordance with the present invention provides an advantage that it is possible to readily and rapidly measure the longitudinal modulus of elasticity of a single fiber at various temperatures including room temperature by using only a single fiber.

Figure 5:
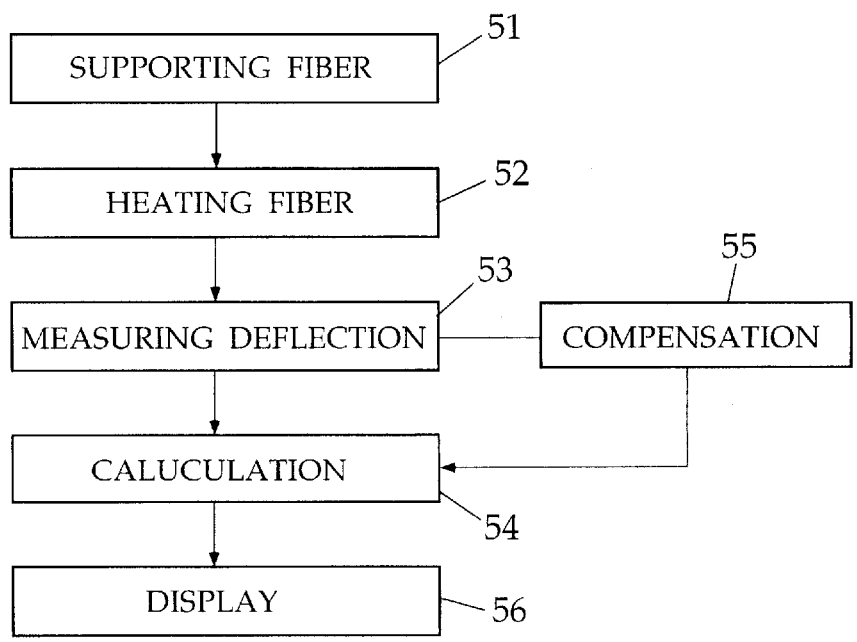
FIG. 5 is a flowchart showing the respective steps of a method of measuring a longitudinal modulus of elasticity of a fiber.

FIG. 5 shows respective steps of the method of measuring the longitudinal modulus of elasticity of a fiber. First, there is prepared an apparatus 10 as illustrated in FIG. 1. A single fiber 1 is supported at its one end with a fiber holder 12 in a cantilever fashion in step 51. The single fiber 1 is kept in a heater 14 consisting of a closed container having a transparent window 14a, and is gradually heated in step 52. Then, the deflection of the single fiber 1 is measured by a laser displacement gauge 16 through the transparent window 14a in step 53.

Signals representing the measured deflection of the single fiber 1 are transmitted to a calculator 18, which calculates the longitudinal modulus of elasticity of the single fiber 1 in accordance with the above mentioned equations (1) to (4), provided that the single fiber 1 is equivalent to a beam receiving uniformly distributed load thereon based on dead weight thereof.

If the single fiber has an initial deformation "a" as illustrated in FIG. 3A, compensation therefore is carried out in step 55 before forwarding to step 54. A signal representing the deflection $Y_1$ measured when a plane containing the single fiber 1 therein vertically stands, as illustrated in FIG. 3A, is transmitted to the calculator 18 from the laser displacement gauge 16. Then, a signal representing the deflection $Y_2$ measured when a plane containing the single fiber 1 therein vertically stands, but is rotated by 180 degrees, as illustrated in FIG. 3B, is also transmitted to the calculator from the gauge 16. A compensator 20 disposed in the calculator 18 calculates an average Δ of the deflections in accordance with the equation (5). The calculated average Δ is returned back to the calculator 18, which then calculates a longitudinal modulus of elasticity E of the single fiber in accordance with the equations (1) to (4). The calculation result is displayed at a screen 19 in step 56.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. An apparatus for measuring a longitudinal modulus of elasticity of a fiber used for composite material, comprising:
   a holder for supporting a single fiber at its one end in a cantilever fashion;
   a heater for heating said single fiber;
   a measurement device for measuring deflection of said single fiber; and
   a calculator for calculating the longitudinal modulus of elasticity of said single fiber in accordance with said deflection measured by said measurement device, provided that said single fiber is equivalent to a beam receiving uniformly distributed load thereon based on dead weight thereof.

2. The apparatus as set forth in claim 1, wherein said heater includes a closed container for heating said single fiber therein, said closed container having a transparent window through which the deflection of said single fiber is measured by said measurement device.

3. The apparatus as set forth in claim 1, wherein said measurement device is a laser displacement gauge.

4. The apparatus as set forth in claim 1, wherein said measurement device is an optical displacement gauge.

5. The apparatus as set forth in claim 2, wherein said closed container is filled with inert gas.

6. The apparatus as set forth in claim 1, wherein said calculator includes a compensator for compensating for initial deformation of said single fiber.

7. The apparatus as set forth in claim 6, wherein said compensator eliminates the initial deformation of said single fiber by defining the deflection Δ of said single fiber in accordance with the following equation:

$$\Delta = (Y_1 + Y_2)/2$$

wherein $Y_1$ represents deflection of said single fiber measured when a plane containing said single fiber therein makes an angle A degrees with a vertical direction, and $Y_2$ represent deflection of said single fiber measured when said plane makes an angle (A+180) degrees with a vertical direction.

8. The apparatus as set forth in claim 7, wherein said angle A is set to be 0 degree.

9. A method of measuring a longitudinal modulus of elasticity of a fiber used for composite material, comprising the steps of:

(a) supporting a single fiber at its one end in a cantilever fashion;

(b) heating said single fiber;

(c) measuring deflection of said single fiber; and (d) calculating a longitudinal modulus of elasticity of said single fiber in accordance with said deflection measured in said step (c), provided that said single fiber is equivalent to a beam receiving uniformly distributed load thereon based on dead weight thereof.

10. The method as set forth in claim 9, wherein said single fiber is heated in said step (b) in a closed container having a transparent window through which deflection of said single fiber can be visually measured.

11. The method as set forth in claim 9, wherein deflection of said single fiber is measured by means of a laser displacement gauge.

12. The method as set forth in claim 9, wherein deflection of said single fiber is measured by means of an optical displacement gauge.

13. The method as set forth in claim 10 further comprising the step (e) of filling said closed container with inert gas before measuring deflection of said single fiber.

14. The method as set forth in claim 9 further comprising the step (f) of compensating for initial deformation of said single fiber, said step (f) being to be carried out subsequently to said step (d).

15. The method as set forth in claim 14, wherein said initial deformation of said single fiber is eliminated in said step (f) by defining deflection $\Delta$ of said single fiber in accordance with the following equation:

$$\Delta = (Y_1 + Y_2)/2$$

wherein $Y_1$ represents deflection of said single fiber measured when a plane containing said single fiber therein makes an angle A degrees with a vertical direction, and $Y_2$ represent deflection of said single fiber measured when said plane makes an angle (A+180) degrees with a vertical direction.

16. The method as set forth in claim 15, wherein said angle A is pre-set to be 0 degree.

* * * * *